US007805173B2

(12) United States Patent
Reeves et al.

(10) Patent No.: US 7,805,173 B2
(45) Date of Patent: Sep. 28, 2010

(54) TAPE MANUFACTURING SYSTEM

(75) Inventors: Jodi L. Reeves, Guilderland, NY (US);
Yunfei Qiao, Schenectady, NY (US)

(73) Assignee: Superpower, Inc., Schenectady, NY (US)

( * ) Notice: Subject to any disclaimer, the term of this patent is extended or adjusted under 35 U.S.C. 154(b) by 695 days.

(21) Appl. No.: 11/560,269

(22) Filed: Nov. 15, 2006

(65) Prior Publication Data
US 2007/0093376 A1     Apr. 26, 2007

Related U.S. Application Data

(62) Division of application No. 10/730,961, filed on Dec. 9, 2003, now Pat. No. 7,146,034.

(51) Int. Cl.
*H01B 12/00* (2006.01)
*H01L 39/00* (2006.01)
*B32B 9/00* (2006.01)

(52) U.S. Cl. .................. 505/230; 505/239; 505/237; 428/702

(58) Field of Classification Search ................ 428/698, 428/701–702; 505/230, 239
See application file for complete search history.

(56) References Cited

U.S. PATENT DOCUMENTS

| 3,825,351 | A | 7/1974 | Seki et al. |
| 3,971,956 | A | 7/1976 | Jakeman |
| 4,079,482 | A | 3/1978 | Yeh |
| 4,110,047 | A | 8/1978 | Takahashi |
| 4,145,140 | A | 3/1979 | Fujii |
| 4,247,907 | A | 1/1981 | Durbeck |
| 4,281,342 | A | 7/1981 | Ueda |
| 4,290,698 | A | 9/1981 | Milana |
| 4,344,127 | A | 8/1982 | McDaniel |

(Continued)

FOREIGN PATENT DOCUMENTS

EP     0 284 630 A1     10/1988

(Continued)

OTHER PUBLICATIONS

"Tropel Lasercheck Non-Contact Surface Roughness," Corning Tropel Corporation, 2 pages; date unknown.

(Continued)

*Primary Examiner*—Stanley Silverman
*Assistant Examiner*—Kallambella Vijayakumar
(74) *Attorney, Agent, or Firm*—Larson Newman & Abel, LLP

(57) ABSTRACT

A tape manufacturing system and a tape-surface-inspection unit are disclosed. The tape-surface-inspection unit is capable of continuously characterizing the surface of a non-transparent tape that is usable with or without a tape manufacturing system. The tape-surface-inspection unit includes a surface illuminator, an imager, an image processor, a tape guide, and, optionally, an indexer. The surface illuminator provides a tape surface located by the tape guide in a manner that allows the imager to capture images for characterization by the image processor. The indexer facilitates a correlation of locations along the tape and a characterization of the locations on the tape. The tape manufacturing system, in addition to at least one tape-surface-inspection unit, includes a tape-processing unit, a tape handler, and a controller.

8 Claims, 9 Drawing Sheets

U.S. PATENT DOCUMENTS

| | | | |
|---|---|---|---|
| 4,396,976 A | 8/1983 | Hyatt |
| 4,449,052 A | 5/1984 | Krieg |
| 4,646,223 A | 2/1987 | Sekiguchi |
| 4,661,001 A | 4/1987 | Takai |
| 4,671,663 A | 6/1987 | Sick |
| 4,673,818 A | 6/1987 | Guerra |
| 4,675,730 A | 6/1987 | Adomaitis et al. |
| 4,836,680 A | 6/1989 | Troster et al. |
| 4,889,367 A | 12/1989 | Miller |
| 4,916,600 A | 4/1990 | Ropelato |
| RE33,387 E | 10/1990 | Binnig |
| 4,978,219 A | 12/1990 | Bessho |
| 5,153,418 A | 10/1992 | Batterman |
| 5,170,044 A | 12/1992 | Pastor |
| 5,189,292 A | 2/1993 | Batterman |
| 5,189,490 A | 2/1993 | Shetty |
| 5,288,986 A | 2/1994 | Pine et al. |
| 5,289,004 A | 2/1994 | Okada |
| 5,296,693 A | 3/1994 | Hughes-Hartogs |
| 5,298,731 A | 3/1994 | Ett |
| 5,304,787 A | 4/1994 | Wang |
| 5,334,844 A | 8/1994 | Pollard et al. |
| 5,351,200 A | 9/1994 | Impink, Jr. |
| 5,355,001 A | 10/1994 | Fujimoto |
| 5,357,094 A | 10/1994 | Baldwin |
| 5,383,776 A | 1/1995 | Trail et al. |
| 5,412,980 A | 5/1995 | Elings |
| 5,468,945 A | 11/1995 | Huggett |
| 5,519,212 A | 5/1996 | Elings |
| 5,526,116 A | 6/1996 | de Groot |
| 5,563,401 A | 10/1996 | Lemelson |
| 5,579,218 A | 11/1996 | Ehlig |
| 5,608,527 A | 3/1997 | Valliant |
| 5,643,368 A | 7/1997 | Nakashima |
| 5,689,415 A | 11/1997 | Calotychos |
| 5,726,912 A | 3/1998 | Krall, Jr. |
| 5,739,086 A | 4/1998 | Goyal |
| 5,741,377 A | 4/1998 | Goyal |
| 5,742,172 A | 4/1998 | Yasutake |
| 5,760,300 A | 6/1998 | Kajimura |
| 5,828,449 A | 10/1998 | King et al. |
| 5,872,080 A | 2/1999 | Arendt |
| 5,898,020 A | 4/1999 | Goyal |
| 5,898,106 A | 4/1999 | Babcock |
| 5,956,134 A | 9/1999 | Roy et al. |
| 5,958,599 A | 9/1999 | Goyal |
| 5,964,966 A | 10/1999 | Goyal |
| 5,980,078 A | 11/1999 | Krivoshein |
| RE36,488 E | 1/2000 | Elings |
| 6,022,832 A | 2/2000 | Fritzemeier |
| 6,027,564 A | 2/2000 | Fritzemeier |
| 6,032,861 A | 3/2000 | Lemelson |
| 6,055,446 A | 4/2000 | Kroeger et al. |
| 6,106,615 A | 8/2000 | Goyal |
| 6,156,376 A | 12/2000 | Paranthaman |
| 6,190,752 B1 | 2/2001 | Do et al. |
| 6,236,044 B1 | 5/2001 | Chou et al. |
| 6,246,054 B1 | 6/2001 | Toda |
| 6,248,009 B1 | 6/2001 | Ito |
| 6,331,199 B1 | 12/2001 | Goyal |
| 6,339,047 B1 | 1/2002 | Christopherson et al. |
| 6,383,989 B2 | 5/2002 | Jia |
| 6,426,320 B1 | 7/2002 | Fritzemeier |
| 6,427,345 B1 | 8/2002 | Alvis |
| 6,447,714 B1 | 9/2002 | Goyal |
| 6,451,450 B1 | 9/2002 | Goyal |
| 6,458,223 B1 | 10/2002 | Hans Thieme |
| 6,475,311 B1 | 11/2002 | Fritzemeier |
| 6,543,691 B1 | 4/2003 | Lemelson et al. |
| 6,562,761 B1 | 5/2003 | Fritzemeier |
| 6,599,346 B2 | 7/2003 | Goyal |
| 6,602,313 B2 | 8/2003 | Goyal |
| 6,607,838 B2 | 8/2003 | Goyal |
| 6,607,839 B2 | 8/2003 | Goyal |
| 6,610,413 B2 | 8/2003 | Goyal |
| 6,610,414 B2 | 8/2003 | Goyal |
| 6,610,632 B2 | 8/2003 | Honjo |
| 6,623,607 B1 | 9/2003 | Stollenwerk |
| 6,654,121 B1 | 11/2003 | Jeong et al. |
| 6,921,741 B2 * | 7/2005 | Arendt et al. ............... 505/239 |
| 2004/0018394 A1 | 1/2004 | Jia et al. |
| 2004/0023077 A1 * | 2/2004 | Jia et al. .................... 428/701 |
| 2004/0206952 A1 | 10/2004 | Jia et al. |

FOREIGN PATENT DOCUMENTS

| | | |
|---|---|---|
| WO | WO 01/56128 A2 | 8/2001 |
| WO | WO 03/082566 A | 10/2003 |

OTHER PUBLICATIONS

"diEnviroScope ATomic Force Microscope," 2003 Veeco Instruments, Inc., 2 pages; date unknown.

"Atomic Force Microscopy for Nan-Surface Tecture/Roughness," Pacific Nanotechnology, Inc., 3 pages; date unknown.

"Using the Dimension X3D AFM in Advanced Photomask Metrology," 2003 Veeco Instruments, Inc., 6 pages; date unknown.

* cited by examiner

TAPE MANUFACTURING SYSTEM

CROSS-REFERENCE TO RELATED APPLICATION(S)

The present application is a divisional application of U.S. application Ser. No. 10/730,961, filed Dec. 9, 2003, now U.S. Pat. No. 7,146,034 which is incorporated herein by reference in its entirety.

The present invention relates generally to tape manufacturing systems and, more particularly, to a tape-surface-inspection unit capable of continuously characterizing the surface of a non-transparent tape and usable in a tape manufacturing system.

BACKGROUND

Manufacturing a non-transparent tape, such as, for example, a metal tape that may be used as a substrate for a high-temperature superconductor (HTS) coated conductor, involves uncoiling a coiled tape, performing an operation with the tape, and recoiling the processed tape. Examples of operations that may be performed may include rolling, texturizing, polishing, cleaning, and a variety of coating operations. Rolling involves creating a tape having an appropriate thickness. Texturizing may be used to create a tape having an appropriate epitaxial template for creating a high-temperature superconductor material over the length of the tape. Cleaning involves removing undesirable features, such as, for example, foreign particulate matters, oils and solvents. Polishing involves creating a tape having an appropriate surface quality. Precoating, as an alternative to texturizing, may be used to create a tape having an appropriate epitaxial template for creating a high-temperature superconductor material over the length of the tape. Coating involves creating a high-temperature superconductor material over the length of the tape. Recoating may be used to encapsulate the high-temperature superconductor material.

It would be desirable to assure that a tape possesses an appropriate surface quality prior to processing so that the processing yields the desired product. Also, it would be desirable to monitor the surface quality during processing to understand that the desired product may be yielded. Furthermore, it would be desirable to characterize the surface quality after processing to understand that the desired product has been yielded.

Some surface quality characterization techniques for metal tapes involve operations that adversely affect the tape integrity. For example, destructive analysis involves cutting sections of a tape, characterizing the section and inferring the quality of the entire length of the tape on the basis of the several sections. There are at least two problems with this approach: the inference can create a false result that may result in good product being set aside and bad product released for further processing and destructively removing sections is counter to the goal of creating long continuous sections of tape.

Other surface quality characterization techniques, although an improvement over destructive analysis, are only capable of determining surface quality when the tape is stationary. These operations involve a repetition of advancing, stopping and observing the tape surface. This repetition is time-consuming, and, therefore, inefficient and cost ineffective. Also, this repetition is incompatible with the advantages associated with continuous processing of tapes.

Thus, there remains a need for a new and improved tape manufacturing system that is capable of continuously processing a tape while at the same time including a tape-surface-inspection unit capable of continuously characterizing the surface of the non-transparent tape.

BRIEF SUMMARY OF INVENTION

The present invention meets these and other needs by providing a tape manufacturing system including a tape-processing unit, a tape handler, at least one tape-surface-inspection unit and a controller. The tape handler provides at least one tape to the tape-processing unit for processing. The controller is at least in communication with the tape-processing unit, the tape handler, and the tape-surface-inspection unit. Thus, at least one tape-surface-inspection unit is capable of continuously characterizing the surface of the at least one tape provided to the tape-processing unit.

The tape-surface-inspection unit includes a surface illuminator, an imager, an image processor, a tape guide, and, optionally, an indexer. The surface illuminator illuminates a tape surface. The imager captures images of the illuminated tape surface. The image processor processes the images of the tape surface so as to allow the characterization of the tape surface. The tape guide locates the tape with respect to the imager. The indexer facilitates a correlation between a location along the tape and a characterization of the location on the tape.

Applicants have found that the indexer may be a scanner based system such as the type that scans for a fudicial mark. Examples of usable fudicial marks include, without limitation, a matrix of dots, alphanumeric indicia, barcode and combination thereof.

A variety of imagers are contemplated including, without limitation, a camera, a microscope, and a human operator. A digital camera has been found to work well and, more particularly a color digital camera. Although a human operator may use a microscope, Applicants believe that augmenting the microscope with a camera is beneficial. Again, the camera may be a digital camera and a color digital camera may provide advantages.

It is desirable that the image processor, whether a device or a human operator, further include one or more of a data storage device, a data indexer, an image data analyzer and a data output. The data indexer facilitates the retrievable storage of image data.

The image data analyzer may include a characteristic identifier. The characteristic identifier is capable of identifying and, optionally, categorizing surface features such as, for example, particles on the surface (surface particles) of the tape, scratches in the surface (surface scratches) of the tape or grain size of the material comprising the surface of the tape. When categorizing surface particles, the characteristic identifier is capable of determining at least surface particle aerial density, surface particle linear density, surface particle size and a combination thereof. Likewise, when categorizing surface scratches, the characteristic identifier is capable of determining at least scratch size, scratch shape, scratch orientation, scratch aerial density, scratch linear density, and combinations thereof.

A data output of the image processor may provide data in any one form of raw data, analyzed data, and combinations thereof. Examples of the types of data that the data output may provide include, without limitation, pictorial data, graphical data, numerical data, and combinations thereof. One example of graphical data includes a histogram of a density of a feature (characteristic density). Examples of numerical data include area fraction of a feature (feature area fraction), and characteristics relating to the grains of the material comprising the surface of the tape (e.g., standardized grain size, average grain size, grain size distribution, monomodal grain size distribution, multimodal grain size distribution, grain shape, grains per square millimeter area, number of grains per unit volume, and average grain volume).

The tape guide may perform any of a number of functions that assist the tape-surface-inspection unit with its function. For example, tape guide may be field of view guide, a focal position guide, and combinations thereof. As a field of view guide, the tape guide locates the tape in the field of view of the imager. As a focal position guide, the tape guide locates the tape surface in the focal position of the imager. To that end, it may be said that the focal position guide is a distance guide. In addition, the focal position guide may be a flatness conditioner for maintaining the tape surface substantially flat.

As a portion of the tape guide may be in contacting communication with the tape, a composition of the material comprising that portion is selected to be compatible with the composition of the tape so as to not cause defects to the tape. To that end, a composition is selected so as to be non-contaminating to the tape while at the same time the composition is selected so as to be non-deforming of the material comprising the tape. Applicants believe that polymers such as the fluorocarbons would work well for such contacting communication and have found polytetrafluoroethylene polymers (some are commercially available under the trademark TEFLON®) to work well.

The surface illuminator may be any source of electromagnetic radiation that is provided in a manner so as to permit characterizing the nature of the surface of the tape. The portion of the electromagnetic radiation spectrum provided to the surface is compatible with that portion to which the imager is sensitive. Applicants believe that the portion of the electromagnetic spectrum that is visible to the human eye is appropriate. To that end, the illuminator may be a light source providing electromagnetic radiation in the optical spectrum (visible light or visible spectrum between about 380 to 780 nanometers).

Applicants have found that it is beneficial that the provided electromagnetic radiation be adjustable with respect to the intensity of the radiation and the angle of incidence. Thus, having the ability to adjust the intensity of the electromagnetic radiation provided by the illuminator is desirable. Concerning the angle of incidence, different angles facilitate observing different features. For example, when the angle of incidence of the electromagnetic radiation provided by a light source is substantially normal to the tape surface, particles are preferably detected. In contrast when the incident electromagnetic radiation provided by a light source is substantially oblique to the tape surface, scratches are preferably detected. Oblique angle between about 10 to 20 degrees with respect to the plane of the tape surface appear to facilitate better scratch detection. Thus, to detect the presence of the variety of surface characteristics, the electromagnetic radiation is provided as a combination of angles of incidence such that at least some is provided substantially normal to the tape surface and another is provided substantially oblique to the tape surface. The illuminator may be a light source. To that end, Applicants have found that the light source may be one or more of a ring light and a gooseneck light (fiber optic bundle).

Whether the tape-surface-inspection unit is used with or without a tape manufacturing system, a controller may be used. As part of the tape manufacturing system, the controller communicates with some or all, as may be appropriate, of the components (e.g., tape handler, tape-processing unit, tape-surface-inspection unit and any other components as may be appropriate) of the system. Those skilled in the art will appreciate that each component may include a subcontroller that may communicate with the controller. Communications between the tape handler and the controller may regulate the rate at which the tape is provided. Likewise, communications between the tape-processing unit and the controller may regulate the residence time of the tape in the tape-processing unit. Further, the controller may communicate that the tape is either acceptable or unacceptable for further manufacturing.

Applicants contemplate that the tape-processing unit of the tape manufacturing system may include any of a variety of operations that may be performed in creating a tape, preparing it for further manufacture and completing a tape's manufacture. Examples of such operations include, without limitation, a polishing operation, a rolling operation, a coating operation, a cleaning operation and combination thereof. When the tape-processing unit is a polishing operation, it may be any one of a mechanical polishing operation, a chemical polishing operation, an electrical polishing operation and combination thereof. Also, when the tape-processing unit is a rolling operation, it may be the rolling operation either alone or further including a texturizing unit. One non-limiting example of a texturizing unit is a heat-treating unit.

Also note above, the tape-processing unit may be a coating operation. Numerous coating operations are contemplated including, without limitation, a physical coating operation, a chemical coating operation, and combination thereof. Any of the preceding may be an ion beam-based coating operation. An example of a physical coating operation is a physical vapor deposition operation optionally including an ion beam source to facilitate the formation of a particular phase and/or morphology in the deposited coating. For example, the ion beam source may facilitate the formation of epitaxial coatings on the tape. An example of a chemical coating operation is a chemical vapor deposition operation and a more specific example is a metalorganic chemical vapor deposition (MOCVD) operation.

Those skilled in the art will appreciate that that the cleaning operation may be any of the number known in the art. When preparing a substrate for a HTS coated conductor, the cleaning operation includes any of those that may remove solvents and particulates used in the manufacture and conditioning of the tape as a substrate. For example, one cleaning operation may involve the removal of residual oils introduced to the surface during rolling, texturizing, or heat treating the tape. Another cleaning operation may involve the removal of residual polishing compounds and fluids from the surface of the tape.

Whether the tape-surface-inspection unit is used with or without a tape manufacturing system, a tape handler may be used. Any of a variety of tape handlers may be used while one that is a tape translation mechanism appears to work sufficiently well. Examples of tape translation mechanisms include, without limitation, a reel-to-reel unit, a conveyor, a robotic translator and combinations thereof.

Accordingly, one aspect of the present invention is to provide a tape manufacturing system including a tape-processing unit, a tape handler, and at least one tape surface inspection unit. The tape handler provides at least one tape to the tape-processing unit for processing. The tape-surface-inspection unit includes a surface illuminator, an imager, an image processor, and a tape guide. The surface illuminator illuminates a tape surface. The imager images the illuminated tape surface. The image processor processes the tape surface image so as to allow the characterization of the tape surface. The tape guide locates the tape with respect to the imager.

Another aspect of the present invention is to provide a tape-surface-inspection unit capable of continuously inspecting a tape. The tape-surface-inspection unit includes a surface illuminator, an imager, an image processor, a tape guide, and an indexer. The surface illuminator illuminates the tape surface. The imager captures images of the illuminated tape surface. The image processor processes the tape surface image so as to allow the characterization of the tape surface. The tape guide locates the tape with respect to the imager. The indexer facilitates a correlation between a location along the tape and a characterization of the location on the tape.

Still another aspect of the present invention is to provide a tape manufacturing system including a tape-processing unit, a tape handler, at least one tape surface inspection unit and a controller. The tape handler provides at least one tape to the tape-processing unit for processing. The controller is at least in communication with the tape-processing unit, the tape handler, and the tape-surface-inspection unit. The at least one tape-surface-inspection unit is capable of continuously characterizing the surface of the at least one tape provided to the tape-processing unit. The tape-surface-inspection unit includes a surface illuminator, an imager, an image processor, a tape guide, and an indexer. The surface illuminator illuminates a tape surface. The imager captures images of the illuminated tape surface. The image processor processes the tape surface images so as to allow the characterization of the tape surface. The tape guide locates the tape with respect to the imager. The indexer facilitates a correlation between a location along the tape and a characterization of the location on the tape.

These and other aspects, advantages, and salient features of the present invention will become apparent from the following detailed description, the accompanying drawings, and the appended claims.

DETAILED DESCRIPTION

Figure 1:
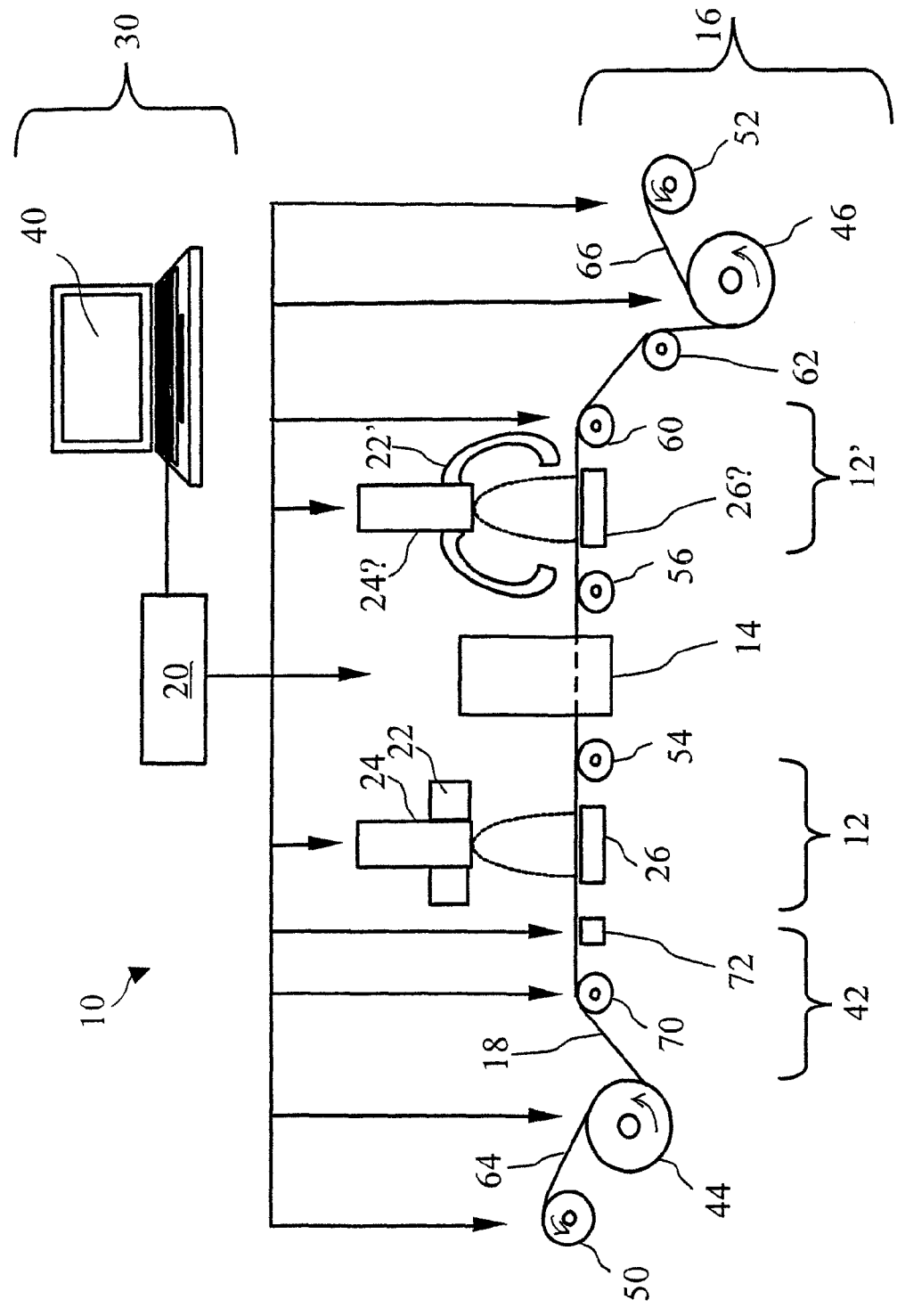
FIG. 1 is a schematic of a tape manufacturing system according to an embodiment of the present invention.

In the following description, like reference characters designate like or corresponding parts throughout the several views shown in the figures. It is also understood that terms such as "top," "bottom," "outward," "inward," and the like are words of convenience and are not to be construed as limiting terms.

Referring to the drawings in general and to FIG. 1 in particular, it will be understood that the illustrations are for the purpose of describing a preferred embodiment of the invention and are not intended to limit the invention thereto. FIG. 1 shows a tape manufacturing system 10 according to the present invention. The tape manufacturing system 10 includes a processing unit 14, a tape handler 16, at least one tape-surface-inspection unit 12, and a controller 20.

Figure 2:
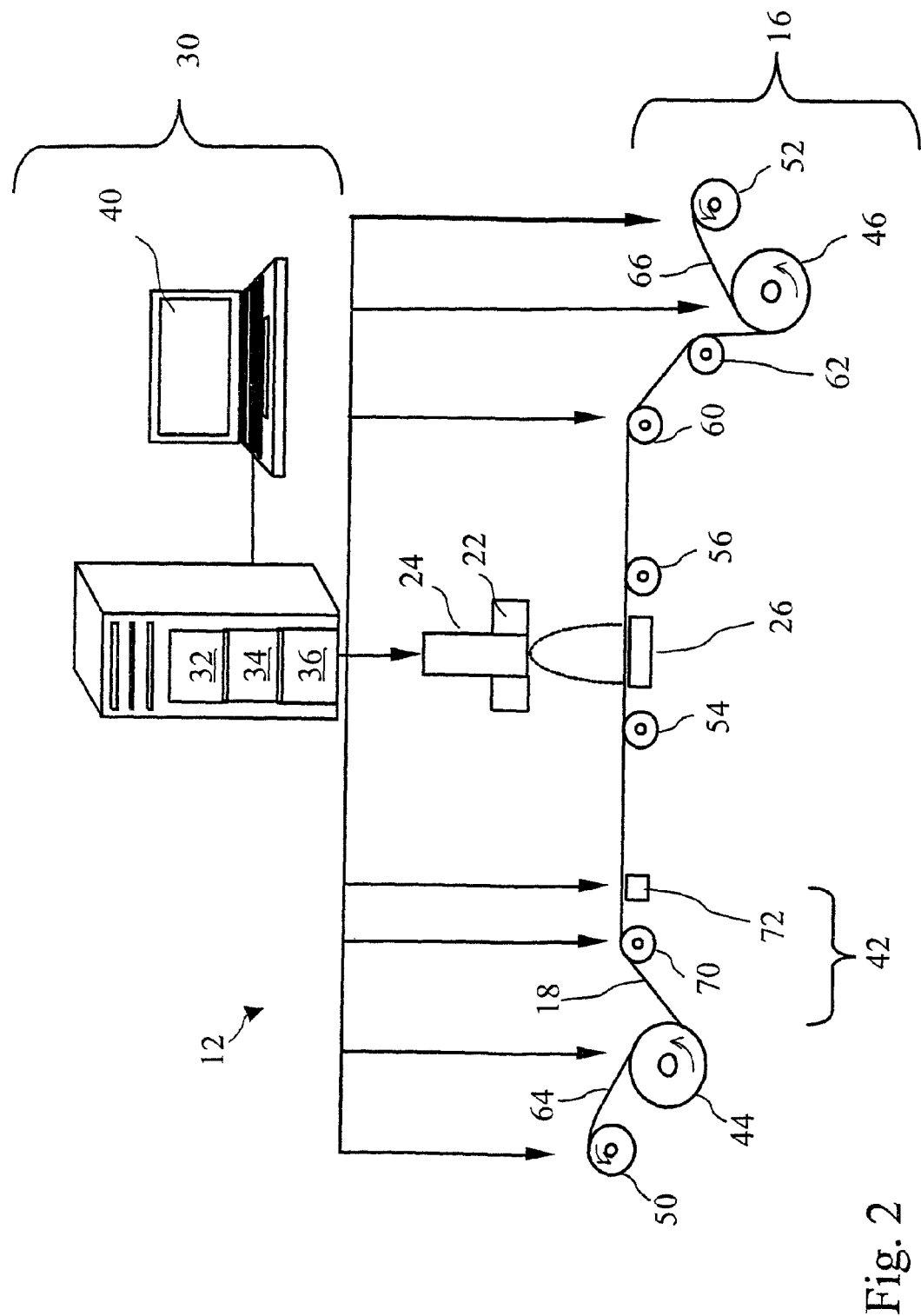
FIG. 2 is a schematic of a tape-surface-inspection unit useable with a tape manufacturing system of FIG. 1 according to an aspect of the present invention.

As may be seen in both FIGS. 1 and 2, a tape-surface-inspection unit 12 includes a surface illuminator 22, an imager 24, a tape guide 26, and an image processor 30. The tape guide 26 is for positioning the tape 18 with respect to the imager 24 and the surface illuminator 22. The surface illuminator 22, imager 24, and tape guide 26 of a tape-surface-inspection unit 12 cooperate to facilitate the characterization of a tape surface as a tape 18 and the imager 24 are moved with respect to each other.

Incorporating a tape-surface-inspection unit 12 in a tape-manufacturing system 10 as shown in FIG. 1 permits a real-time examination and characterization of any flexible non-transparent tape-like structure to provide processing control during its manufacture, in accordance with the present invention. A tape-surface-inspection unit 12 as shown in FIG. 2 permits a real-time examination and characterization of any flexible non-transparent tape-like structure, such as a metal substrate tape used in the manufacture of HTS-coated conductor, in accordance with the present invention.

Examples of a flexible non-transparent tape-like structure that may be inspected in a tape-surface-inspection unit 12 of the present invention include, without limitation, a substrate such as any of those disclosed in U.S. Pat. Nos. 6,610,632; 6,541,121; 6,383,989 and 5,872,080; U.S. Pat. Nos. 6,610,414; 6,610,413; 6,607,839; 6,607,838; 6,602,313; 6,599,346; 6,451,450; 6,447,714; 6,331,199; 6,156,376; 6,106,615; 5,964,966; 5,958,599; 5,898,020; 5,741,377 and 5,739,086; and U.S. Pat. Nos. 6,562,761; 6,475,311; 6,458,223; 6,426,320; 6,027,564; and 6,022,832 (the disclosure of each being hereby incorporated by reference in their entirety). It will be appreciated by those skilled in the art that the tape is non-transparent with respect to the preselected portion of the electromagnetic radiation spectrum being provided to the surface of the tape. That is, the tape is incapable of transmitting or impermeable to electromagnetic radiation of specified frequencies so that objects or images cannot be seen as there is the intervening material. In contrast, a transparent tape is capable of transmitting or permeable to electromagnetic radiation of specified frequencies so that objects or images can be seen by an appropriate corresponding device sensitive to the electromagnetic radiation of specified frequencies as if there were no intervening material. Thus, for example a metal tape while being non-transparent when that preselected portion of the electromagnetic radiation spectrum is the optical portion of the spectrum may be transparent when the preselected portion of the electromagnetic radiation spectrum is the x-ray portion of the spectrum. Likewise, an optically transparent polymer tape while being transparent when the preselected portion of the electromagnetic radiation spectrum is the optical portion of the spectrum may be non-transparent when the preselected portion of the electromagnetic radiation spectrum is that portion of the spectrum to which the optically transparent polymer tape is not permeable.

The tape handler 16 of the tape-manufacturing system 10 of FIG. 1 and the tape-surface-inspection unit 12 of FIG. 2 includes a payout spool 44, which is located at the entry point of each, and upon which is wound a length of tape 18. The tape 18 is subsequently threaded through each and then wound onto a take-up spool 46 located at the exit point. For the manufacture of HTS-coated conductor, the tape 18 is formed of metals, such as stainless steel or a nickel alloy such as INCONEL®, that are capable of withstanding high temperatures and vacuum conditions. The tape 18 is typically between about 3 to about 60 millimeters (mm) in width and upwards of several hundred meters in length. Applicant contemplates that the tape 18 may be any width between about 1 mm and 100 mm. After processing, a tape 18 may be sliced to into a plurality if tapes having lesser widths. For example, an about 60 mm wide processed tape may be sliced in a manner that produces four about 15 mm wide tapes. In a like manner, an about 12 mm wide processed tape may be sliced in a manner that produces four about 3 mm wide tapes. Thus, Applicants contemplate that the tape 18 may include any width between 1 and 100 mm, such as for example 4 mm, 5 mm, 10 mm, 11 mm, 12 mm, 98 mm and 99 mm. The tape 18 typically has several meters of "leader" at both ends to aid in handling.

If a barrier 64 is interleafed with the tape 18 upon the payout spool 44, as the tape 18 unwinds from the payout spool 44 the barrier 64 unwinds onto a take-up spool 50 that is located in close proximity to the payout spool 44. Similarly as the tape 18 winds upon the take-up spool 46, a barrier 66 may be interleaved with the tape 18. A payout spool 52 located proximate to the take-up spool 46 supplies the barrier 66. The barriers 64 and 66 are protective tapes having compositions that protect the surface of the tape 18 from, for example, scratching and denting. Composition that may work for barriers 64 and 66 may include metallic and/or organic interleafing materials. Some examples of organic compositions include polyester or polyimide compositions. Some such materials are commercially available as MYLAR®) polyester film from DuPont Teijin Films and KAPTON® polyimide film from DuPont High Performance Materials. The dimensions of barrier 64 and barrier 66 correspond to those of the tape 18.

A conventional stepper or AC vector drive motor may be used to drive the payout spool 44. In other applications, AC motors (synchronous or variable frequency) or DC motors (brushed, brushless serve) and drives may be used. The motor is selected to be capable of providing the required translation speed of the tape 18. Also, the motor has the ability to move the tape 18 in user-specified increments and to reverse the direction of the tape 18. The take-up spool 50, the take-up spool 46, and the payout spool 52 each may be driven by a conventional torque motor that assists in providing the proper tension to the tape 18 as it translates through the tape-manufacturing system 10 or tape-surface-inspection unit 12 when used alone.

An encoder 70, which is part of indexer 42, is located at the entry point just downstream of the payout spool 44. The encoder 70 provides position tracking and also monitors the translation rate of the tape 18 as it translates through the tape-manufacturing system 10 or tape-surface-inspection unit 12 when used alone. The encoder 70 can be of multiple types, such as a Model #92205-0409F-5L01-A24SP-04EK manufactured by Gurley Precision Instruments (Troy, N.Y.). The encoder 70 also may serve as an idler or guide wheel upon which the tape 18 rides as it unwinds from the payout spool 44.

A scanner 72, which is part of indexer 42, is located just downstream of the encoder 70. The scanner 72 provides a capability for detecting an identifying mark, such as the Job number and location ID, that is on the back surface of the tape 18. The scanner 72 is, for example, a barcode or a dot matrix ID scanner, such as a Model BL-600 manufactured by Keyence. The purpose of the scanner is to allow data logging of specific feature information based on the Job number and location ID to enable tracking of that identical location on the tape 18 at later operations. Applicants contemplate that any of a number of known method, structures and apparatuses may be used including, without limitation, those disclosed in U.S. Pat. Nos. 6,543,691; 6,032,861; 5,563,401; 5,468,945; 5,357,094; 5,355,001; 5,304,787; 5,298,731; 5,296,693; 5,288,986; 5,189,292; 5,170,044; 5,153,418; 4,889,367; 4,661,001; 4,449,052; 4,247,907; 4,281,342; and 4,079,482 (the disclosure of each being hereby incorporated by reference in their entirety).

Referring now to FIG. 1, the tape-manufacturing system 10 further includes a first guide 26 located just downstream of the scanner 72, followed by a tape processing unit 14, followed by a second guide 26'. Also positioned in various locations along the path of travel of the tape 18 is a plurality of idlers that are part of the tape handler 16. In the example shown in FIG. 1, an idler 54 is located just downstream of the guide 26, an idler 56 is located just downstream of the tape processing unit 14, a load cell 60 followed by an idler 62 are located just downstream of the guide 26' and just prior to the take-up spool 46. The idlers 54, 56, and 62 serve as guide wheels upon which the tape 18 may ride and, along with the torque motors of the payout spool 44 and the take-up spool 46, assist in providing the proper tension to the tape 18 as it translates through the tape-manufacturing system 10. The idlers 54, 56, and 62 are formed of a material that is not damaging to the surface of the tape 18, such as polyethylene polymers having an ultra high molecular weight (UHMW-PE, a molecular weight in the range of 3,000,000 to 6,000,000), polytetrafluoroethylene polymers (some are commercially available under the trademark TEFLON®), ceramic coatings or soft rubber. The dimensions of the idlers 54, 56, and 62 are in accordance with the dimensions of the tape 18 translating through the tape-manufacturing system 10. The load cell 60 provides feedback of the tension of the tape 18 so that constant and uniform tension is maintained throughout the change in tape spool diameter on the payout spool 44.

The tape guides 26 and 26' are formed of a material that is not damaging (e.g., non-contaminating and non-deforming) to the surface of the tape 18 such as UHMW-PE or polytetrafluoroethylene polymers. The guides 26 and 26' provide positional stability to the tape 18 as it rides over the surface of the guides 26 and 26' while the surface illuminators 22 and 22' provide a preselected portion of the electromagnetic radiation spectrum to the surface of the tape 18 and imagers 24 and 24' capture images thereof. Two aspects with respect to location of guides 26 and 26' and imagers 24 and 24' appear to be notable. One is the guides 26 and 26' acting as field of view guides and the other is the guides 26 and 26' acting as focal position guides. A focal position guide operates to set the distance of the tape 18 from the imager 24 so that the tape 18 is within the field of view of the imager 24, as well as or in addition to, conditioning the tape so that it is flat with respect to the field of view of the imager 24. The dimensions of the guides 26 and 26' are in accordance with the dimensions of the tape 18 translating through the tape-manufacturing system 10.

In the manufacture of HTS-coated conductors, it is desirable to have the capability to monitor a number of features of the surface of a tape 18 and, when possible, characterize these features. Some example of features (and their size or source) include water marks (about 10 μm), tiny particles (<10 μm), foreign particles (e.g., dust particles, particles from polishing processes), long and short unidirectional scratches (e.g., caused by the polishing process), random scratches (e.g., caused by handling), large and small scale waviness and bending, (e.g., caused by the manufacturer of the tape 18 or a polishing process), dents (e.g., those incurred on a very thin portion of the tape 18), burrs (e.g., those incurred on an edge of the tape 18), inconsistent polishing defects (e.g., defects caused by non-uniform polishing), inclusions in the tape 18, and features relating the grain size of the tape 18. It is desirable that the tape surface inspection unit 12 of FIG. 2 and the tape surface inspection unit 12 used in the tape manufacturing system 10 in FIG. 1 are capable of identifying and characterizing some or all of the above listed features.

Surface illuminators 22 and 22' may be any source of electromagnetic radiation that is provided in a manner so as to permit characterizing the nature of the surface of the tape 18. The portion of the electromagnetic radiation spectrum provided to the surface is compatible with that portion to which the imager 24 is sensitive. When characterizing the surface of a tape 18 such as non-transparent metal substrate used in the manufacture of HTS-coated conductor, Applicants have found that an illuminator 22 providing that portion of the electromagnetic spectrum that is visible to the human eye is appropriate. To that end, illuminators 22 and 22' may be a light source providing electromagnetic radiation in the optical spectrum (visible light or visible spectrum between about 380 to 780 nanometers).

Different angles of incidence of the provided electromagnetic radiation facilitate observing different features. Also, different intensities of the provided electromagnetic radiation facilitate observing different features. For example, when a light source is used as one of the surface illuminators 22 and 22' and the angle of incidence of the light is substantially normal to the surface of the tape 18, particles are preferably detected. In contrast when the light is provided substantially oblique to the surface of the tape 18, scratches are preferably detected. Oblique angles between about 10 to about 20 degrees with respect to the plane of the surface of the tape 18 appear to facilitate better detection of scratches in light. To that end, Applicants have found that it is beneficial that the surface illuminators 22 and 22' be adjustable with respect to the intensity and the angle of incidence at which electromagnetic radiation may be provided. To detect the presence of the variety of surface features, the electromagnetic radiation is provided as a combination of angles of incidence such that at least some is provided substantially normal to the tape surface and at least another portion is provided substantially oblique to the tape surface.

The surface illuminators 22 and 22' of FIGS. 1 and 2 may be light sources. The schematic for surface illuminator 22 may represent a ring light (e.g., model No.: LS-150 by Brook-Anco Corp.) while the schematic for surface illuminator 22' may represent a gooseneck light (e.g., model No.: Schott KL 200 light source with any of single, dual models, or combination assemblies of goosenecks and/or flexible light guides available from EOI Inc.).

The imagers 24 and 24' may be any appropriate commercially available cameras such as, for example, charge-coupled device (CCD) cameras, combined with an appropriate lens or mounted to light microscopes (not shown). The CCD cameras are conventional digital cameras capable of providing a two-dimensional image, such as a Model 3.2.0 manufactured by Diagonistics Instruments, Inc. Examples of appropriate lens or light microscopes are zoom lens or light microscope objectives with a typical magnification of up to about 200×. However, the resolution and magnification may vary by the imager 24 type, lens type or objectives type that are used and user's requirements. The typical resolution of the imagers 24 and 24' is such that defects greater than or equal to about 10 microns in size are visible in the images taken by the imagers 24 and 24'. The combination of the resolution and magnification determines the defect size that is visible in the imagers 24 and 24'. The imagers 24 and 24' are focused on the surface of the tape 18 at the point where the tape 18 rides over the surface of the guides 26 and 26', respectively.

The tape-processing unit 14 may be any of a variety of operations that may be performed in creating a tape 18, preparing it for further manufacture and completing a tape 18 manufacture. Examples of such operations include, without limitation, a polishing operation, a rolling operation, a coating operation, a cleaning operation or combination thereof. When the tape-processing unit 14 is a polishing operation, it may be any one of a mechanical polishing operation, a chemical polishing operation, an electrical polishing operation and combination thereof. Also when the tape-processing unit 14 is a rolling operation, it may be the rolling operation either alone or further including a texturizing unit. One non-limiting example of a texturizing unit is a heat-treating unit.

As noted above, the tape-processing unit 14 may be a coating operation. Numerous coating operations are contemplated including, without limitation, a physical coating operation, a chemical coating operation, and combination thereof. Any of the preceding may be an ion beam-based coating operation. An example of a physical coating operation is a physical vapor deposition operation optionally including an ion beam source to facilitate the formation of a particular phase and/or morphology in the deposited coating. For example, the ion beam source may facilitate the formation of epitaxial coatings on the tape 18. An example of a chemical coating operation is a chemical vapor deposition operation and a more specific example is a metalorganic chemical vapor deposition (MOCVD) operation.

With respect to rolling operations, any number of a variety is contemplated. For example, a manufacturer of metal tapes may use the tape-manufacturing system 10 of the present invention to provide quality-controlled tape 18 that forms the substrate for HTS conductors. Examples of tape 18, and the attendant methods and materials, include those disclosed in U.S. Pat. Nos. 6,610,632; 6,541,121; 6,383,989 and 5,872, 080 (the disclosure of each being hereby incorporated by reference in their entirety). To that end, both tapes 18 with and without a barrier layer are contemplated in the current invention. With respect to a barrier layer, the tape 18 may be manufactured and/or inspected to verify that it would not have undesirable features, such as scratches, etc. With respect to non-barrier tapes, the tape 18 may be manufactured and/or inspected to verify that it has an appropriate texture to act as a seed for the formation of a high temperature conducting material of HTS conductors. In this case, the processing unit 14 could be a texturizer such a heating treating unit so as to heat treat the tape 18 to have the appropriate grain sizes and/or orientation.

Examples of texturizers, and the attendant methods and materials, include those disclosed in U.S. Pat. Nos. 6,610,414; 6,610,413; 6,607,839; 6,607,838; 6,602,313; 6,599,346; 6,451,450; 6,447,714; 6,331,199; 6,156,376; 6,106,615; 5,964,966; 5,958,599; 5,898,020; 5,741,377 and 5,739,086 by Goyal et al. and U.S. Pat. Nos. 6,562,761; 6,475,311; 6,458,223; 6,426,320; 6,027,564; and 6,022,832 by Fritzemeier et al. (the disclosure of each being hereby incorporated by reference in their entirety).

Those skilled in the art will appreciate that the cleaning operation may be any of the number known in the art. When preparing to be a substrate for a high-temperature superconductor coated conductor, the cleaning operation may include those that remove solvents and particulates used in the manufacture and conditioning of the tape 18 as a substrate. For example, one cleaning operation may involve that removal of residual oils introduced to the surface during rolling, texturizing, or heat treating the tape 18. Another cleaning operation may involve that removal of residual polishing compounds and fluids from the surface of the tape 18.

For example, when tape-processing unit 14 of FIG. 1 is a cleaning operation, it removes foreign matter (e.g., debris, dust, residual manufacturing, polishing, and cleaning fluids) from the surface of the tape 18 using a cleaning solution, such as acetone or methanol. The tape-processing unit 14 may be an automated or manual cleaning operation. In a manual cleaning operation, an operator cleans the tape 18 using, for example, a cloth POLX® 1200 cleanroom wipe or non-abrasive tissue. An automated cleaning station may be one such as that manufactured by METFAB Technologies. Optionally, a dryer may be part of or placed downstream from the cleaning operation.

As shown in FIG. 1, the tape-manufacturing system 10 includes a controller 20 in communication with the processing unit 14, tape handler 16, tape-surface-inspection units 12, and their subcomponents directly or through their subcontrollers or both. For the tape-surface-inspection units 12, this is shown as lines drawn from the controller 20 to the encoder 70 and scanner 72 of the indexer 42, the surface illuminator 22, the imager 24, and the image processor 30. For the tape handler 16 this is shown as lines drawn from the controller 20 to the payout spool 44, take-up spool 50, the load cell 60, the payout spool 52 and the take-up spool 46. The controller 20 controls the overall operation of the tape-manufacturing system 10. The controller 20 may be, for example, a personal computer (PC) with the appropriate control software. The image processor 30 may be stand-alone or may be integral with the controller 20. In either case, image processor 30 includes digital imaging and analysis software, and data output 40 such as a monitor for viewing digital images. An example of the analysis software is "analySIS" by Software Imaging System, Corp.

As shown in further detail in FIG. 2, the image processor 30 includes a data storage device 32, a data indexer 34 for retrieving stored images, an image data analyzer 36, and a data output 40. As reference was made to above, the image data analyzer 36 includes a feature identifier such as digital imaging and analysis software. Such software desirably is capable of identifying and, optionally, categorizing surface features, such as, for example, water marks, tiny particles, foreign particles, long and short unidirectional scratches, random scratches, large and small scale waviness and bending, dents, burrs inconsistent with polishing defects, inclusions in the tape 18, and features relating the grain size of the tape 18. When categorizing surface particles, the characteristic identifier is capable of determining at least surface particle aerial density, surface particle linear density, surface particle size and combination thereof. Likewise when categorizing surface scratches, the characteristic identifier may be capable of determining at least scratch size, scratch shape, scratch orientation, scratch aerial density, scratch linear density, and combination thereof.

The data storage device 32 is capable of storing either the raw or analyzed data. Also, the data output device 40 is capable of presenting either the raw or analyzed data. The data output device 40 associated with the image processor 30 may provide data in any one form of raw data, analyzed data, and combinations thereof. Examples of the types of data that the data output may provide include, without limitation, pictorial data, graphical data, numerical data, and combinations thereof. One example of graphical data includes a histogram of a density of a feature (feature density). Examples of numerical data include area fraction of a feature (feature area fraction), and characteristics relating to the grains of the material comprising the surface of the tape (e.g., standardized grain size, average grain size, grain size distribution, monomodal grain size distribution, multimodal grain size distribution, grain shape, grains per square millimeter area, number of grains per unit volume, and average grain volume).

In operation of either tape-surface-inspection units 12 alone or in combination with the tape-manufacturing system 10, a user first activates the translation of the tape 18 by the tape handler 16, via the controller 20, by activating the payout spool 44, the take-up spool 50, the load cell 60, the take-up spool 46, and the payout spool 52. Next, the user activates, via the controller 20, the encoder 70 and the scanner 72 of the indexer 42, the tape processing unit 14 (if present and automated). The encoder 70 provides continuous feedback of positional tracking data and translation rate of the tape 18 to the controller 20. The scanner 72 reads the Job # and location ID of the tape 18 and likewise provides feedback to the controller 20. The load cell 60, in combination with the torque motor on take-up spool 46, provides continuous feedback of the tension of the tape 18 to the controller 20.

As an example, a tape-manufacturing system 10 that includes a cleaning operation as the processing unit 14, the controller 20 may be programmed to signal the imager 24, which in this case may be a, to take snapshots of the tape 18 at, for example, between about 1-10-second time intervals. The imager 24 provides continuous feedback of these digital snapshots camera to the controller 20, while the controller 20 is simultaneously storing the positional tracking date associated with each snapshot. The image processor 30 analyzes each image via the imaging analysis software to determine if an undesirable feature (i.e., defect) appears in the photograph of the surface of the tape 18. The analysis software determines, for example, the type of features, its size, and the distance between features present upon the tape 18. As undesirable features are discovered on the surface of the tape 18, the controller 20 uses the positional tracking data to signal the tape-processing unit 14 to activate to clean the area when the undesirable feature area reaches the tape-processing unit 14. The tape 18 thereby experiences a cleaning event within the tape-processing unit 14 at a point on the tape 18 associated with the undesirable feature as photographed by the imager 24 and logged by image processor 30 and/or controller 20. After the tape 18 experiences the cleaning event at the tape-processing unit 14, the imager 24' (in this case also a camera) takes one or more snapshots of the cleaned area of the tape 18 and feeds back to the controller 20, where the images are analyzed to verify that the defect has been successfully removed. If the images retrieved by imager 24' reveal uncleaned undesirable feature on the tape 18, the controller 20 may signal the tape handler 16 comprised of the payout spool 44, the take-up spool 50, the take-up spool 46, and the payout spool 52 to rewind the tape 18 and activate a second cleaning event upon the undesirable feature area within the tape processing unit 14.

Throughout the operation of either tape-surface-inspection units 12 alone or in combination with the tape-manufacturing system 10, information associated with the tape 18 under inspection is logged by either the image processor 30 or the controller 20 or both, such as date of inspection, run number, reel position, spool number, processing run number, tape length, associated point on the tape 18 where undesirable features were analyzed, and overall quality/condition.

The translation rate of the tape 18 through the tape-manufacturing system 10 is determined by the rate of image acquisition by the imagers 24 and 24' (e.g., shutter speed of camera) and the processing rate of the tape-processing unit 14. Alternatively, the translation of the tape 18 is momentarily interrupted while a photograph is taken of the surface of the tape 18 via the imagers 24 and/or 24', or likewise the translation of the tape 18 is momentarily interrupted while the processing event at the tape-processing unit 14 occurs.

In this manner, the tape-manufacturing system 10 of the present invention provides an in-situ, real-time, macro-level examination and characterization system for use with a translating non-transparent metal substrate tape. The imager 24' that is downstream of the processing event provides a quality control mechanism for determining if the tape 18 is sufficiently processed and thus suitable for subsequent processes.

Also, tape-surface-inspection units 12 of the present invention may provide an ex-situ, real-time, macro-level examination and characterization system for use with a translating non-transparent metal substrate tape. More specifically, the tape-surface-inspection units 12 of the present invention are used for characterizing the tape 18 as received from any previous polishing and/or cleaning processes by determining the particle size and quantity of any remaining polishing residue. Additionally, the tape-surface-inspection unit 12 of the present invention is used for examination of the tape 18 for determining the presence of defects and for subsequently providing a cleaning event to remove these defects.

Figure 3:
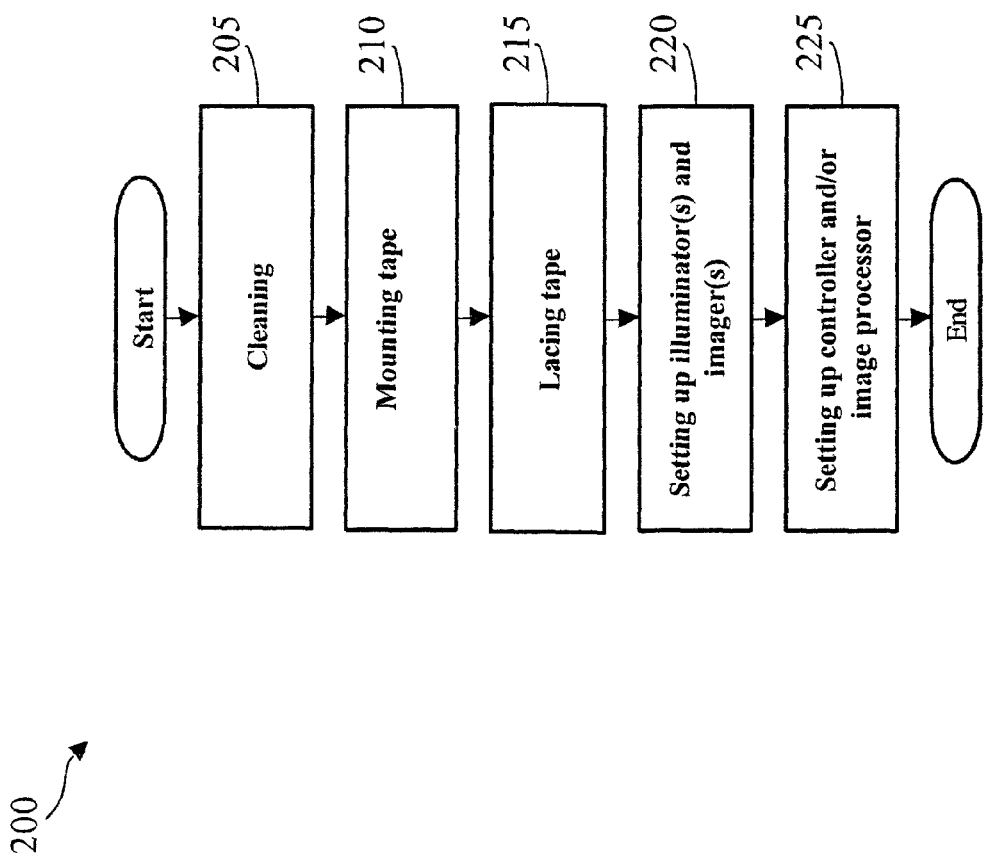
FIG. 3 is a schematic of a block diagram for the method of setting up a tape manufacturing system of FIG. 1; and a tape-surface-inspection unit of FIG. 2.

FIG. 3 is a flow chart illustrating the setting up of either tape-manufacturing system 10 of FIG. 1 of the tape-surface-inspection unit 12 of FIG. 2 that is suitable for either the in-situ or ex-situ inspection and characterization of any flexible tape-like structure, such as a metal substrate tape used in the manufacture of HTS-coated tape. The method 200 includes the steps of:

Step 205, Cleaning: In this step, the operator cleans the points on which a tape 18 mounted in tape-manufacturing system 10 or the tape-surface-inspection unit 12 will come in contact with acetone or isopropanol. The tape-manufacturing system 10 and the tape-surface-inspection unit 12 are locatable in a Class 10,000 or better clean room. The method 200 proceeds to step 210.

Step 210, Mounting tape: In this step, the operator mounts the payout spool 44 holding a tape 18 wound upon it. The operator also places an empty spool in the position of the take-up spool 46. The method 200 proceeds to step 215.

Step 215, Lacing tape: In this step, the operator treads the leader of the tape 18 through all the components of the tape-manufacturing system 10 as illustrated in FIG. 1 or the tape-surface-inspection unit 12 as illustrated in FIG. 2. That is, the leader of the tape 18 is threaded through the encoder 70, the scanner 72, the guide 26, the idler 54, the tape processing unit 14, the idler 56, the guide 26', the load cell 60, and the idler 62, and then onto the take-up spool 46. The tape 18 is mechanically secured upon the take-up spool 46. When used, the barrier 64 is threaded onto the take-up spool 50 and the barrier 66 is interleaved with the tape 18 as it winds upon the take-up spool 46. The tape 18 is allowed to wrap two full rotations upon the take-up spool 46. The tension of the tape 18 is adjusted via the torque motors of the take-up spool 46. The scanner 72 identifies the serial number on the tape 18. The method 200 proceeds to step 220.

Step 220, Setting up illuminator(s) and imager(s): In this step, the illuminators 22 and 22' and imagers 24 and 24' are set up. For example, when using cameras in combinations with microscopes, the operator uncovers the lens of the microscope and subsequently activates the cameras by setting up their light microscope objective, their associated lamps, and focusing the light microscopes and camera to the surface of the tape 18. The method 200 proceeds to step 225.

Step 225, Setting up controller and/or image processor: In this step, the user initiates the software programs on the controller 20 and/or the image processor 30 and takes a sample snapshot of the tape 18 via the imagers 24 and 24'. The resulting images are displayed via the data output 40 and the operator then focuses and adjusts the contrast if necessary. The operator then activates a program, such as "Inspection" by Labview, which is installed on the controller 20 and/or the image processor 30. The method 200 ends.

The controller 20 is a commercially available controller with a plurality of inputs and outputs that meet the requirements of the peripherals. The controller 200 may be a microcontroller or a PC with appropriate hardware and software. Details concerning controllers that may be used in tape-manufacturing system 10 are discussed in, for example, U.S. Pat. Nos. 5,980,078; 5,726,912; 5,689,415; 5,579,218; 5,351,200; 4,916,600; 4,646,223; 4,344,127; and 4,396,976, the entire disclosure of each being incorporated by reference herein.

Figure 4:
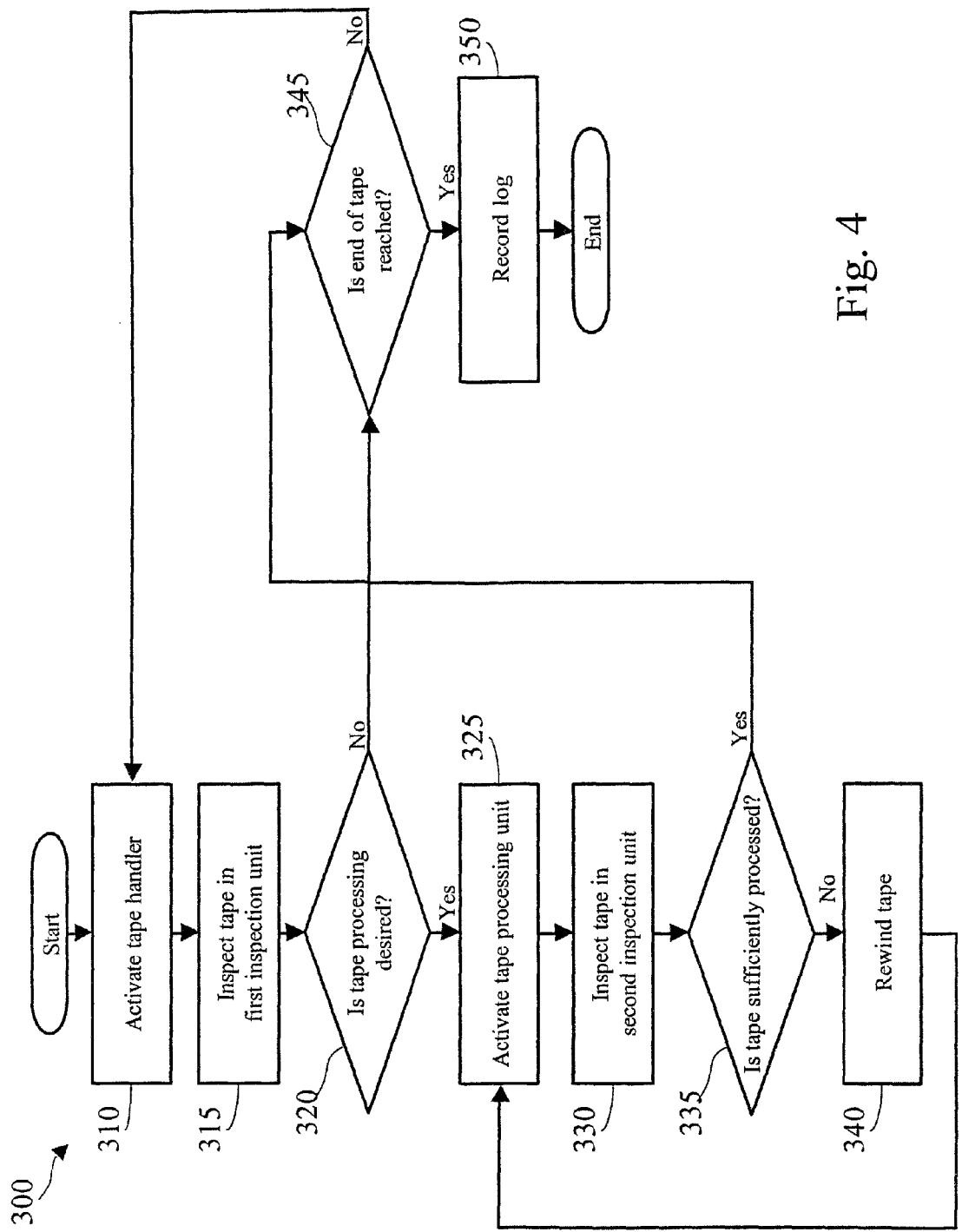
FIG. 4 is a schematic of a control block diagram useable with a tape manufacturing system of FIG. 1 according to an aspect of the present invention.

FIG. 4 is a flow chart illustrating the operation of either tape-manufacturing system 10 of FIG. 1 or the tape-surface-inspection unit 12 of FIG. 2 that is suitable for either the in-situ or ex-situ inspection and characterization of any flexible tape-like structure, such as a metal substrate tape used in the manufacture of HTS-coated tape. The method 300 includes the steps of:

Step 310, Activating tape handler: In this step, via the controller 20, the operator runs a fixed portion (i.e., a length) of the tape 18 through the tape-manufacturing system 10 of FIG. 1 or the tape-surface-inspection unit 12 of FIG. 2. The method 300 proceeds to step 315.

Step 315, Inspecting tape in first inspection unit: In this step, the operator inspects the surface of the tape 18 using illuminators 22 and imagers 24. When the imager 24 is a camera, viewing a 2x-5x magnification of the tape 18 and not using backlighting illuminators 22, appears to provide better results. The method 300 proceeds to step 320.

Step 320, Is tape processing desired?: In this decision step, the operator or limits set in the tape 18 inspection software package determines whether the portion of the tape 18 captured by the image 24 and displayed via the data output 20 contains undesirable features and therefore requires processing. If yes, the operator or analysis software advances the undesirable features of the tape 18 into the tape-processing unit 14 via the tape handler 16 and the method 300 proceeds to step 325. If no, the operator advances the tape 18 onto the take-up spool 46 via the controller 20 and the method 300 proceeds to step 345.

Step 325, Activating tape processing: In this step, the operator or analysis software activates the processing event at the tape processing unit 14 via the controller 20 in order to process the detected undesirable feature area from the surface of the tape 18. The method 300 proceeds to step 330.

Step 330, Inspecting tape in second inspection unit: In this step, the operator or analysis software advances the undesirable feature area and subsequently processed portion of the tape 18 under illuminators 22' and imagers 24' via the tape handler 16. An image of this portion of the tape 18 is taken via the imagers 24' and is displayed via the data output 40 for the operator to again inspect the surface of tape 18. When the imager 24 is a camera, viewing at 2×-5× magnification of the tape 18 and not using backlighting illuminators 22' appears to provide better results. The method 300 proceeds to step 335.

Step 335, Is tape sufficiently processed?: In this decision step, the operator or analysis software determines whether the portion of the tape 18 as displayed via the data output 40 is free of undesired features. If yes, the method 300 proceeds to step 345. If no, the method 300 proceeds to step 340.

Step 340, Rewinding tape: In this step, the operator or analysis software, via the tape handler 16, rewinds the tape 18 such that the undesired features portion of the tape 18 re-enters the tape processing unit 14. The method 300 returns to step 325.

Step 345, Is end of tape reached?: In this decision step, the operator or analysis software determines via the scanner 72 of indexer 42 if the end marker on the tape 18 has been reached. If yes, the method 300 proceeds to step 350. If no, the method 300 returns to step 310.

Step 350, Recording log: In this step, the controller 20 and or the image processor 30 logs the following information for the tape 18, and the method 300 ends.

Figure 5:
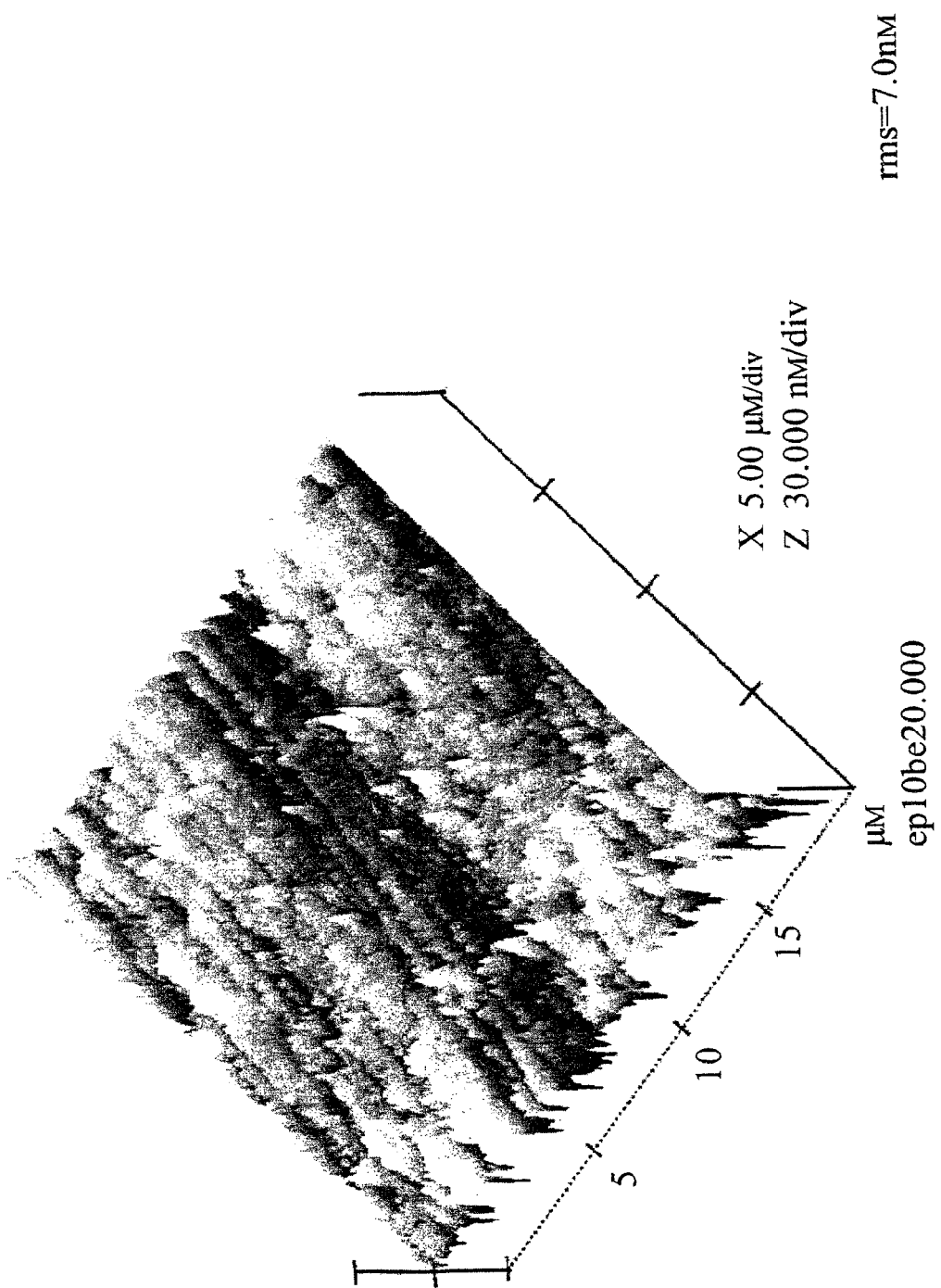
FIG. 5 shows a topographic plot of the surface roughness as measured by means of AFM (Atomic Force Microscope) for an area measuring about 20 micrometer×20 micrometer of a non-transparent tape useable as a substrate in the manufacture of a HTS coated conductor and having a surface roughness of about 7 nanometers (nm) RMS over the area according to an aspect of the present invention.

Date of inspection
Run number
Reel position
Spool number
Polishing run number
Tape length
Quality/condition-defects-size/type/quantities
Location of defects in length of the tape 18 as sensed from the scanner 72 by location ID Turning now to a product that results from the use of the present invention, FIG. 5 shows a topographic plot of the surface roughness measured by means of AFM (Atomic Force Microscope) for an area measuring about 20 micrometer×20 micrometer (20×20 µm) of a non-transparent tape useable as a substrate in the manufacture of a HTS coated conductor and having a surface roughness of about 7 nanometers (nm) RMS over the area according to an aspect of the present invention. The Table below shows the AFM surface roughness measurements of three typical polished non-transparent tapes, labeled EPR10, EPR12, EPR14, prepared using the present invention. For each non-transparent tape, measurements were made using areas measuring about 5×5µ m and about 20×20µ m at the front center, front edge, back center and back edge of the non-transparent tapes. The measurements were made by a commercial vendor that provides such services. Example of vendors providing such services include Pacific Nanotechnology, Inc. of Santa Clara, Calif. and Veeco Metrology Group of Chadds Ford, Pa. Details relating to the measurement of surface roughness using AFM means are included in U.S. Pat. Nos. RE36,488; RE33,387; 6,427,345; 6,246,054; 5,898,106; 5,760,300; 5,519,212; 5,412,980; and 5,289,004 (the disclosure of each being hereby incorporated by reference in their entirety). As is evident from the results presented in the Table, surface roughness measured by means of AFM varied from about 1.0 nm to about 7.0 nm RMS.

|  |  | Epr10 | Epr12 | Epr13 |
|---|---|---|---|---|
| 5 × 5 µm | Front center | 1.7 | 1.8 | 1.7 |
|  | Front edge | 3.6 | 0.5 | 1.2 |
|  | Back center | 4.3 | 1.0 | 1.2 |
|  | Back edge | 2.2 | 1.5 | 1.0 |
| 20 × 20 µm | Front center | 2.9 | 3.7 | 3.1 |
|  | Front edge | 4.0 | 2.0 | 3.2 |
|  | Back center | 7.0 | 4.2 | 3.6 |
|  | Back edge | 7.0 | 3.8 | 2.1 |

Figure 6:
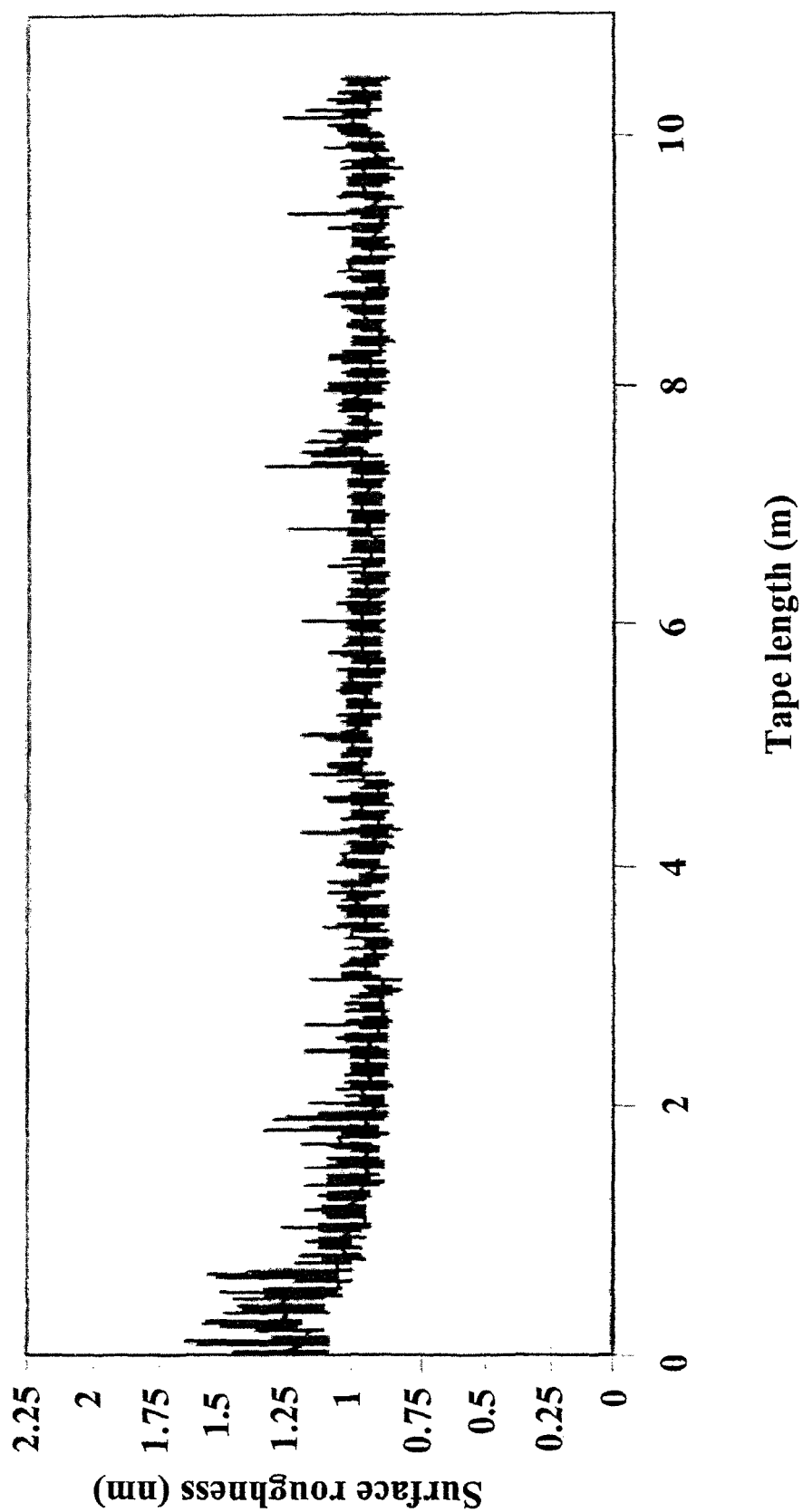
FIG. 6 shows the results of surface roughness measurement measured by means of a laser that gives an average surface roughness of 1 nm over about 10 meters and a range of surface roughness from about 0.8 nm to about 1.6 nm for a non-transparent tape useable as a substrate in the manufacture of a HTS coated conductor according to an aspect of the present invention.

FIG. 6 shows the results of surface roughness measurement measured by means of a laser that gives an roughness average (Ra) of about 1 nm over 10 meters and a range of RMS roughness from about 0.8 nm to about 1.6 of a non-transparent tape useable as a substrate in the manufacture of a HTS coated conductor according to an aspect of the present invention. Such measurements may be made by commercially available equipment such as, for example, the Lasercheck® line of high speed, non-contact surface roughness measurement gages available from Optical Dimensions, LLC of Lake Forest, Calif. and Corning Tropel Corporation of Fairport, N.Y. Details relating to the measurement of surface roughness using a laser means are included in U.S. Pat. Nos. 5,608,527; 5,526,116; 5,189,490; 4,978,219; 4,673,818; 4,290,698; 4,145,140; and 3,971,956 (the disclosure of each being hereby incorporated by reference in their entirety).

Figure 7:
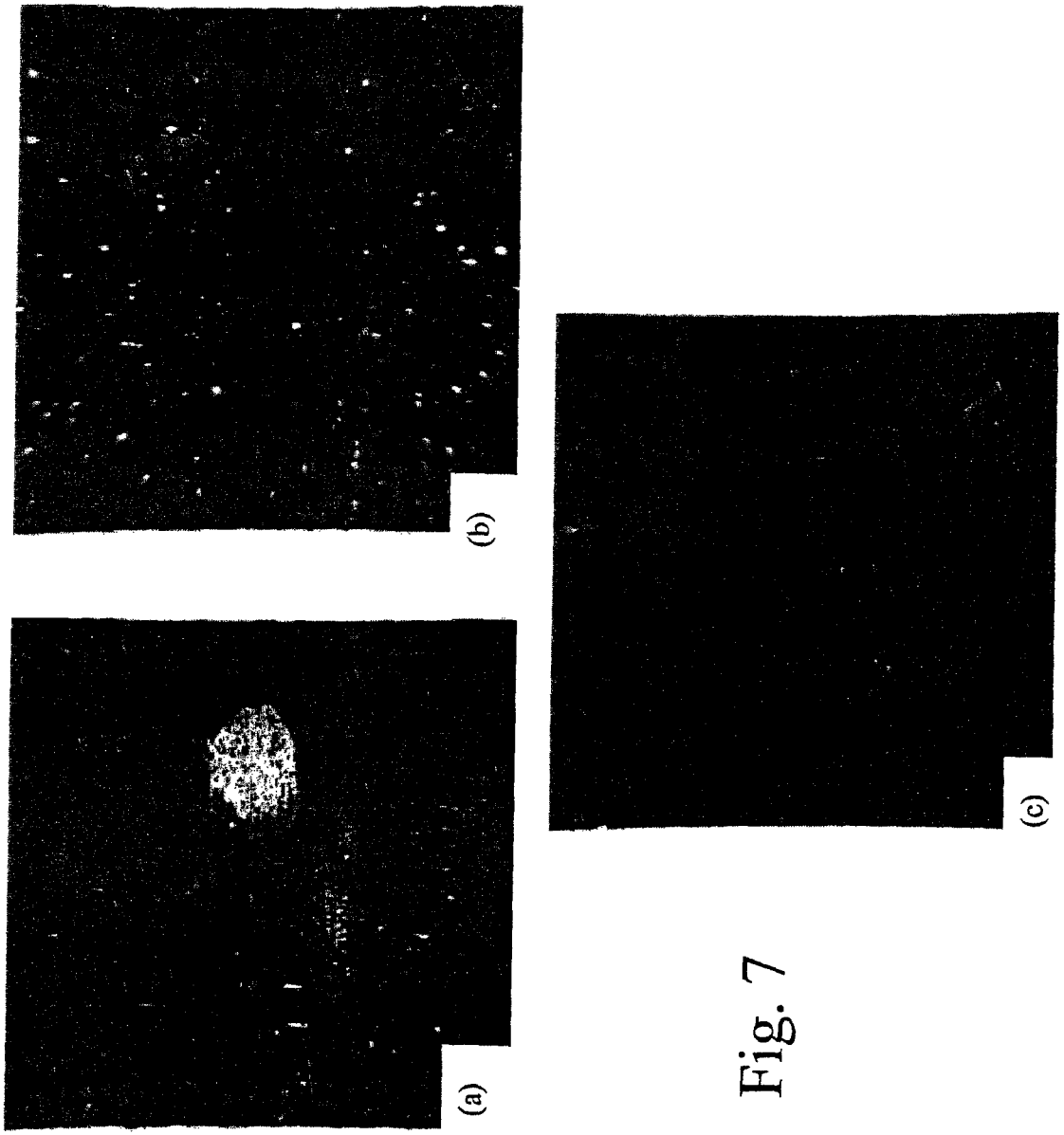
FIG. 7 shows surface imaging of particle density in different regions made using a digital camera with microscope and zoom lens from an about 1 centimeter (cm) wide non-transparent tape useable as a substrate in the manufacture of a HTS coated conductor with a large defect (a), several small particulate defects (b), and particle free region (c) according to an aspect of the present invention.
Figure 8:
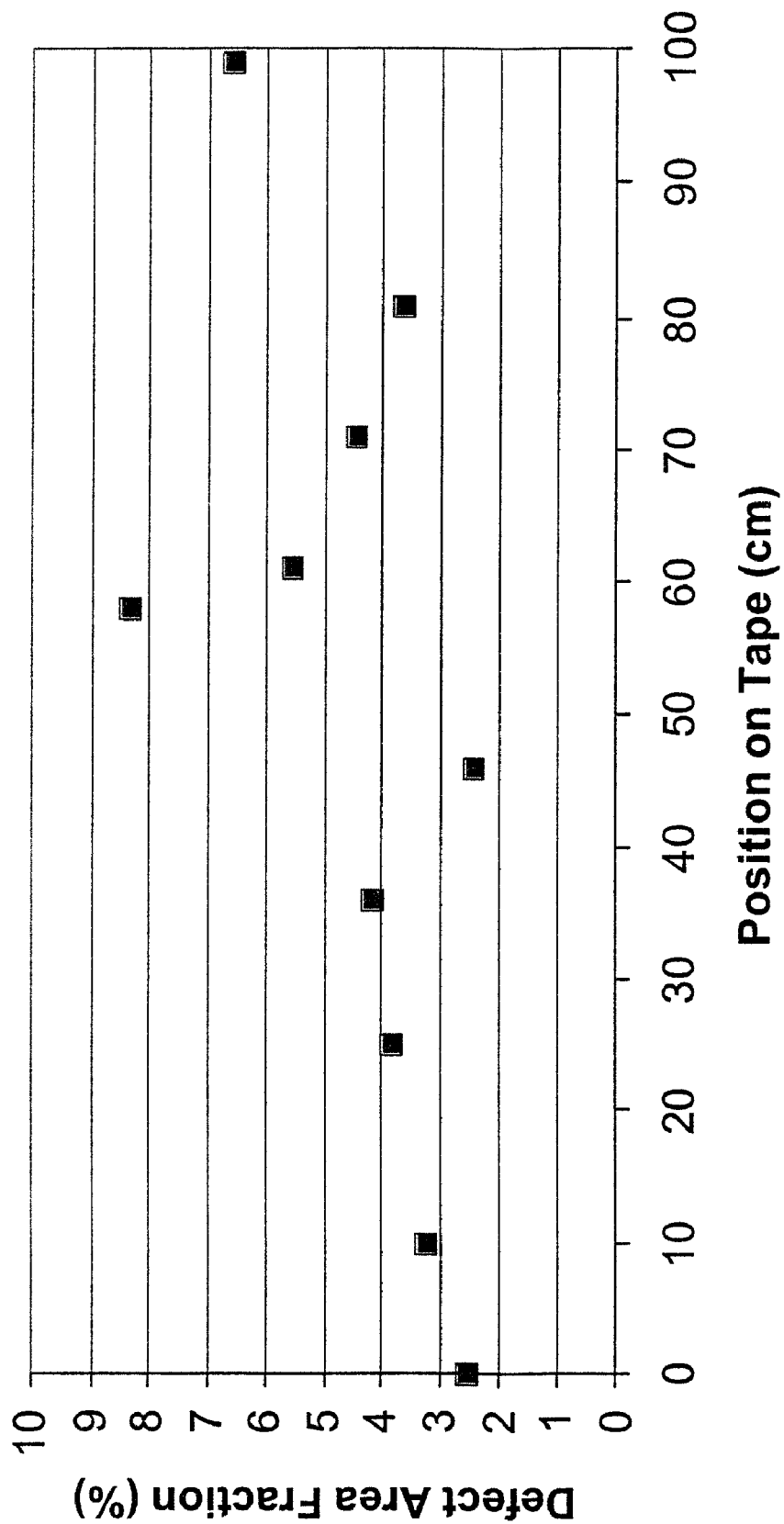
FIG. 8 shows the distribution of defects quantified in terms of area fraction percentage and plotted as a function of position along a one meter long non-transparent tape useable as a substrate in the manufacture of a HTS coated conductor to according an aspect of the present invention.
Figure 9:
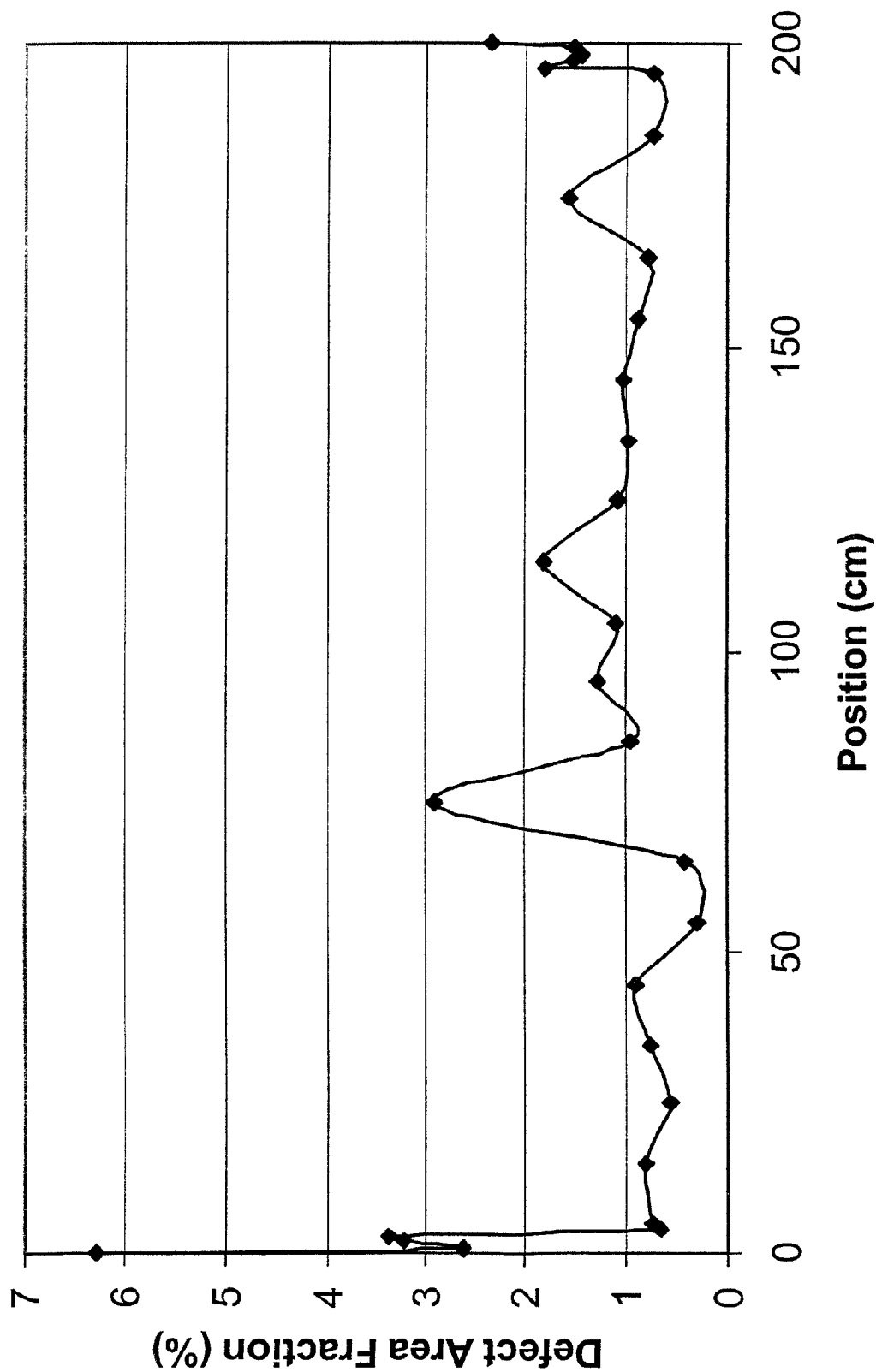
FIG. 9 shows the distribution of defects quantified in terms of area fraction percentage and plotted as a function of position along a two meter long non-transparent tape useable as a substrate in the manufacture of a HTS coated conductor according to an aspect of the present invention.

FIG. 7 shows surface imaging of particle density in different regions made using a digital camera with microscope and zoom lens from an about 1 centimeter (cm) wide non-transparent tape useable as a substrate in the manufacture of a HTS coated conductor with a large defect (a), several small particulate defects (b), and particle free region (c) according to an aspect of the present invention. The images were taken using a digital camera such as a Sony, Nikon, or Spot Insight digital camera. FIG. 8 and FIG. 9 show the distribution of defects quantified in terms of area fraction percentage and plotted as a function of position along a one and two meter long non-transparent tape useable as a substrate in the manufacture of a HTS coated conductor to according an aspect of the present invention. Examples of the software used to quantify the area fraction of defects are Vision image processing software from Clemex, NIH Image from Scion Corporation, and Photoshop by Adobe. These examples show a defect area density ranging from about 0.5 to about 8.5%.

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention. By way of example, more than two cameras could be used, multiple sequences of processing units could be used; different tape tensioning mechanisms could be used. Also, steps in method 200 could be added or deleted.

It should be understood that all such modifications and improvements have been deleted herein for the sake of conciseness and readability but are properly within the scope of the following claims.

The invention claimed is:

1. A non-transparent tape useable as substrate in the manufacture of a high temperature superconducting conductor, said non-transparent tape comprising:
   (a) a surface finish of about 0.1 to about 10 nm RMS; and
   (b) a surface defect area fraction of about 0.5% to about 10%.

2. A non-transparent tape according to claim 1 wherein the tape surface is substantially free of particulates or contamination materials.

3. A non-transparent tape according to claim 1 wherein the surface roughness is measured by means of an Atomic Force Microscope (AFM).

4. A non-transparent tape according to claim 1 wherein the surface roughness is measured by means of laser.

5. A non-transparent tape according to claim 2 wherein the area fraction of defects is quantified by an image processing software.

6. A non-transparent tape according to claim 1, wherein said tape is provided in the form of substrate of a high temperature superconducting conductor, the substrate having a high-temperature superconducting layer disposed thereon.

7. A high temperature superconductor (HTS) coated conductor comprising:
   a non-transparent tape substrate comprising a surface finish of about 0.1 to about 10 nm RMS, and a surface defect area fraction of about 0.5% to about 10%;
   a high temperature superconductor layer overlying the non-transparent tape substrate.

8. The high temperature superconductor (HTS) coated conductor of claim 7, further comprising an epitaxial layer provided between the high temperature superconductor layer and the non-transparent tape substrate.

* * * * *